United States Patent
Lim et al.

(10) Patent No.: US 11,801,192 B2
(45) Date of Patent: Oct. 31, 2023

(54) WALKING ASSISTANCE ROBOT AND METHOD OF CONTROLLING THE WALKING ASSISTANCE ROBOT

(71) Applicant: Samsung Electronics Co., Ltd., Suwon-si (KR)

(72) Inventors: Bok Man Lim, Yongin-si (KR); Kee Hong Seo, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 460 days.

(21) Appl. No.: 16/144,128

(22) Filed: Sep. 27, 2018

(65) Prior Publication Data
US 2019/0021938 A1    Jan. 24, 2019

Related U.S. Application Data

(63) Continuation of application No. 14/498,133, filed on Sep. 26, 2014, now Pat. No. 10,117,801.

(30) Foreign Application Priority Data

Nov. 7, 2013    (KR) .......................... 10-2013-0134784

(51) Int. Cl.
*A61H 3/00*    (2006.01)
*A61H 1/02*    (2006.01)
*A61B 34/30*    (2016.01)

(52) U.S. Cl.
CPC .............. *A61H 3/00* (2013.01); *A61B 34/30* (2016.02); *A61H 1/024* (2013.01); *A61H 1/0244* (2013.01);
(Continued)

(58) Field of Classification Search
CPC ........ A61H 3/00; A61H 1/024; A61H 1/0244; A61H 1/0266; A61H 2201/1215;
(Continued)

(56) References Cited

U.S. PATENT DOCUMENTS

| 8,376,971 B1 | 2/2013 | Herr et al. |
| 2004/0064195 A1* | 4/2004 | Herr .......................... A61F 2/66 623/44 |

(Continued)

FOREIGN PATENT DOCUMENTS

| CN | 102721943 A | 10/2012 |
| CN | 103200909 | 7/2013 |

(Continued)

OTHER PUBLICATIONS

Korean Office Action dated Aug. 28, 2019 for KR Application No. 10-2013-0134784.

(Continued)

*Primary Examiner* — Timothy A Stanis
(74) *Attorney, Agent, or Firm* — HARNESS, DICKEY & PIERCE, P.L.C.

(57) ABSTRACT

Disclosed are a walking assistance robot and a method of controlling the walking assistance robot. The control method includes collecting motion information by sensing or measuring a motion of at least one joint, determining a motion state of the at least one joint based on the sensed or measured motion of the at least one joint, and controlling the walking assistance robot based on the determined motion state of the at least one joint.

15 Claims, 9 Drawing Sheets

(52) U.S. Cl.
CPC ... *A61H 1/0266* (2013.01); *A61H 2201/0176* (2013.01); *A61H 2201/0184* (2013.01); *A61H 2201/1215* (2013.01); *A61H 2201/1246* (2013.01); *A61H 2201/165* (2013.01); *A61H 2201/1676* (2013.01); *A61H 2201/5002* (2013.01); *A61H 2201/5007* (2013.01); *A61H 2201/5058* (2013.01); *A61H 2201/5061* (2013.01); *A61H 2201/5069* (2013.01); *A61H 2201/5079* (2013.01); *A61H 2201/5084* (2013.01)

(58) Field of Classification Search
CPC ...... A61H 2201/1246; A61H 2201/165; A61H 2201/5058
See application file for complete search history.

(56) References Cited

U.S. PATENT DOCUMENTS

| | | | |
|---|---|---|---|
| 2004/0249319 A1* | 12/2004 | Dariush | A61H 3/00 601/5 |
| 2005/0102111 A1* | 5/2005 | Dariush | B25J 9/0006 702/41 |
| 2006/0046907 A1 | 3/2006 | Rastegar et al. | |
| 2006/0293791 A1* | 12/2006 | Dariush | B25J 9/0006 700/245 |
| 2010/0094188 A1 | 4/2010 | Goffer et al. | |
| 2010/0113980 A1* | 5/2010 | Herr | A61F 2/72 600/587 |
| 2010/0114329 A1 | 5/2010 | Easier et al. | |
| 2012/0259431 A1* | 10/2012 | Han | A61H 1/024 623/24 |
| 2012/0310122 A1 | 12/2012 | Endo et al. | |
| 2013/0226048 A1* | 8/2013 | Unluhisarcikli | A61H 1/00 601/34 |
| 2015/0142130 A1* | 5/2015 | Goldfarb | A61H 1/0244 623/25 |

FOREIGN PATENT DOCUMENTS

| | | |
|---|---|---|
| CN | 103263339 A | 8/2013 |
| EP | 1 410 780 A1 | 4/2004 |
| JP | H 08-328627 A | 12/1996 |
| JP | 2003-79684 A | 3/2003 |
| JP | 2005253650 A | 9/2005 |
| JP | 2012-200318 A | 10/2012 |
| KR | 10-2007-0092312 | 9/2007 |
| KR | 1020120134036 A | 12/2012 |
| KR | 10-2013-0056026 | 5/2013 |
| WO | WO-2006/135797 A2 | 12/2006 |
| WO | WO-2006/135797 A3 | 5/2007 |

OTHER PUBLICATIONS

Chinese Office Action dated May 30, 2019 for CN Application No. 201410591857.5.
European Patent Office Communication pursuant to Article 94(3) EPC dated Mar. 13, 2019 for EP Application No. 14 19170.5.
Chinese Office Action dated Dec. 3, 2018 by the National Intellectual Property Administrative, PRC for CN Application No. 201410591857.5.
European Search Report for EP Application No. 14 19 1470 dated Jun. 19, 2015.
Chinese Office Action dated Aug. 31, 2017 by the State Intellectual Property Office of P.R. China for Chinese Application No. 201410591857.5.
Japanese Office Action dated Jan. 23, 2018 for Japanese Patent Application No. 2014-159871 (with English translation).
Office Action issued by the State Intellectual Property Office of P.R. China dated May 15, 2018 for CN Application No. 201410591857.5.
Notice of Allowance issued by the Japanese Patent Office dated Jul. 3, 2018 for Japanese Patent Application No. 2014-159871.
European Patent Office communication dated Mar. 2, 2021 for Application No. 14 191 470.5.
Extended European Search Report dated Apr. 5, 2022 for Application No. EP 22150070.5.
Examination dated May 4, 2023 in European Application No. 22 150 070.5.

* cited by examiner

<br>

WALKING ASSISTANCE ROBOT AND METHOD OF CONTROLLING THE WALKING ASSISTANCE ROBOT

CROSS-REFERENCE TO RELATED APPLICATION

This application is a continuation application of U.S. application Ser. No. 14/498,133, filed on Sep. 26, 2014, which claims priority under 35 U.S.C. § 119 to Korean Patent Application No. 2013-0134784, filed on Nov. 7, 2013 in the Korean Intellectual Property Office, the disclosure of each of which is incorporated herein by reference.

BACKGROUND

1. Field

Example embodiments relate to a walking assistance robot and a method of controlling the walking assistance robot.

2. Description of the Related Art

Walking assistance devices may assist a user who has difficulty in walking, thereby allowing the user to walk more easily. People may have difficulty in walking for innate reasons, such as genetic defects, or acquired reasons, such as age, diseases, accidents, etc. Walking assistance devices are provided to reduce such difficulty in walking.

Examples of walking assistance devices include a walking assistance vehicle provided with at least one wheel and a support board, and a walking assistance robot to assist a user in walking by applying required force to muscles of a human body during walking.

The walking assistance robot may be fixed to the hips, upper leg, shin, etc. of a human body, and assists muscular and joint motions by applying force, e.g., torque to muscles and joints via an actuator and a variety of machinery, thereby assisting a wearer in walking more easily.

SUMMARY

Therefore, some example embodiments provide a walking assistance robot which may appropriately and efficiently assist a user in walking and a method of controlling the walking assistance robot.

Example embodiments will be set forth in part in the description which follows and, in part, will be obvious from the description, or may be learned by practice thereof.

Some example embodiments relate to a walking assistance robot,

In some example embodiments, the walking assistance robot includes at least one joint, a motion information collection unit to sense or measure motion of the at least one joint, and a processing unit to determine a motion state of the at least one joint based on the sensed or measured motion of the at least one joint and to control the walking assistance robot based on the determined result related to the motion state of the at least one joint.

Some example embodiments relate to a method of controlling a walking assistance robot.

In some example embodiments, the method includes collecting motion information by sensing or measuring a motion of at least one joint, determining a motion state of the at least one joint based on the sensed or measured motion of the at least one joint, and controlling the walking assistance robot based on the determined motion state of the at least one joint.

Some example embodiments relate to a method of controlling movement of at least one joint of a walking assistance device.

In some example embodiments, the method includes detecting motion of the at least one joint of the walking assistance device; determining a current walking stage of the walking assistance device based on the motion of the at least one joint, the current walking stage being one of a plurality of walking stages associated with a walking operation; and applying an assistance torque to a limb associated with the at least one joint based on the current walking stage.

In some example embodiments, the assistance torque includes one or more of an active component, a damping component and a dynamic compensation component.

In some example embodiments, the method further includes continually determining whether the at least one joint is exerting positive work on the limb to accelerate the limb or negative work on the limb to decelerate the limb; adjusting the active component of the assistance torque to increase the assistance torque applied to the limb, if the at least one joint is exerting positive work on the limb; and adjusting the damping component of the assistance torque to decrease the assistance torque applied to the limb, if the at least one joint is exerting negative work on the limb.

In some example embodiments, the adjusting the active component includes using determining the active component based on a torque variation pattern, the torque variation pattern calculated based on previously observed motion of the joint, and the adjusting the damping component includes determining the damping component based on an angular velocity of the joint such that a walking speed of the walking assistance device is maintained above a threshold.

In some example embodiments, the walking assistance device is configured to be worn by a user, and the adjusting the active component includes, determining whether the user and the walking assistance device are walking in unison, and increasing the active component, if the walking assistance device and the user are not walking in unison.

In some example embodiments, the method further includes determining a torque variation pattern associated with the current walking stage based on when a joint angle associated with the current walking state is maximum; and applying the assistance torque during the current walking stage based on the torque variation pattern such that the assistance torque varies as a function of time and is less than or equal to a maximum joint torque associated with the current walking stage.

BRIEF DESCRIPTION OF THE DRAWINGS

These and/or other aspects of the example embodiments will become apparent and more readily appreciated from the following description of the embodiments, taken in conjunction with the accompanying drawings of which.

DETAILED DESCRIPTION

Figure 1:
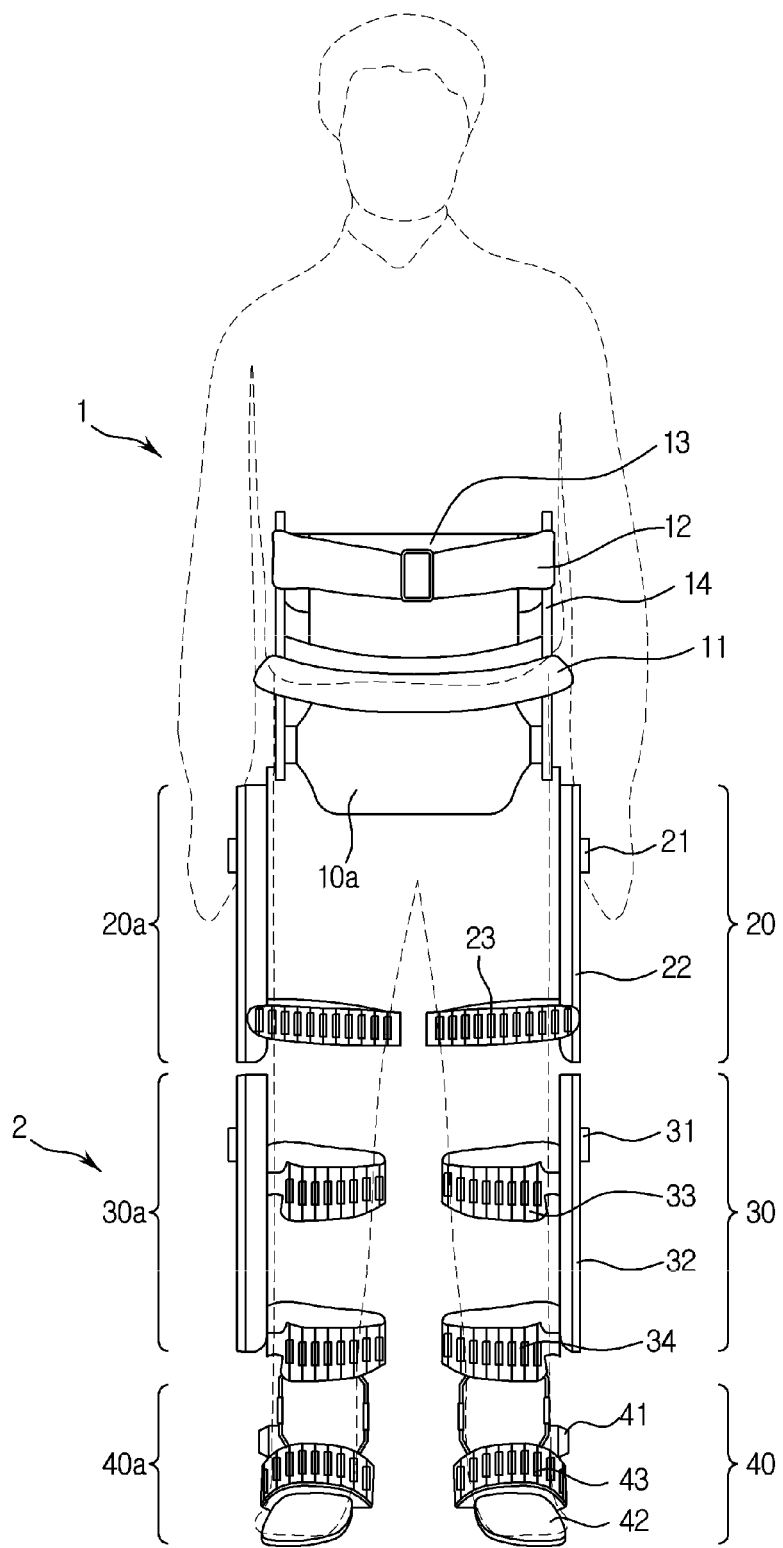
FIG. 1 is a front view showing one embodiment of a walking assistance robot.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Hereinafter, some example embodiment of a walking assistance robot will be described with reference to FIGS. 1 to 6.

Figure 2:
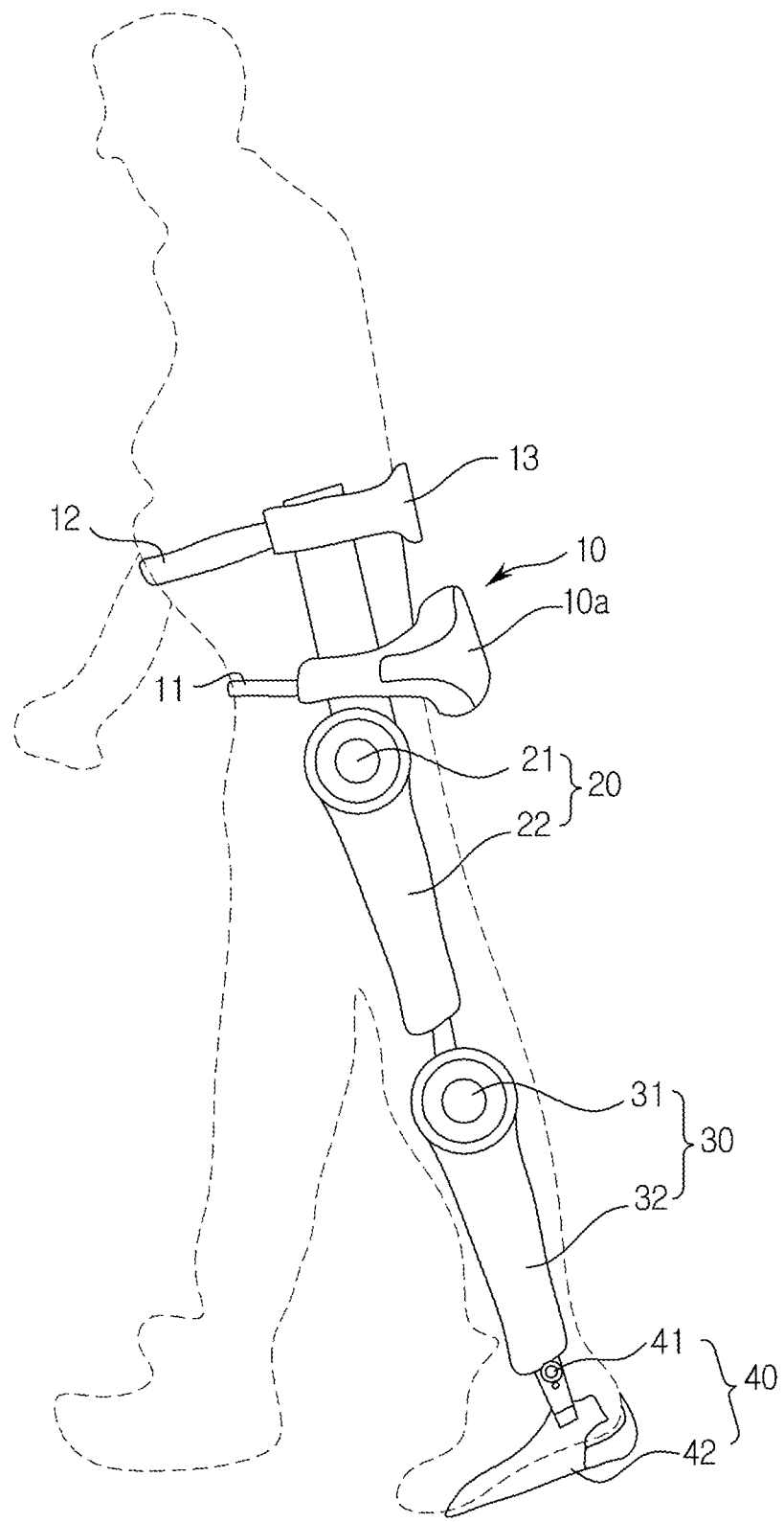
FIG. 2 is a side view showing one embodiment of a walking assistance robot.
Figure 3:
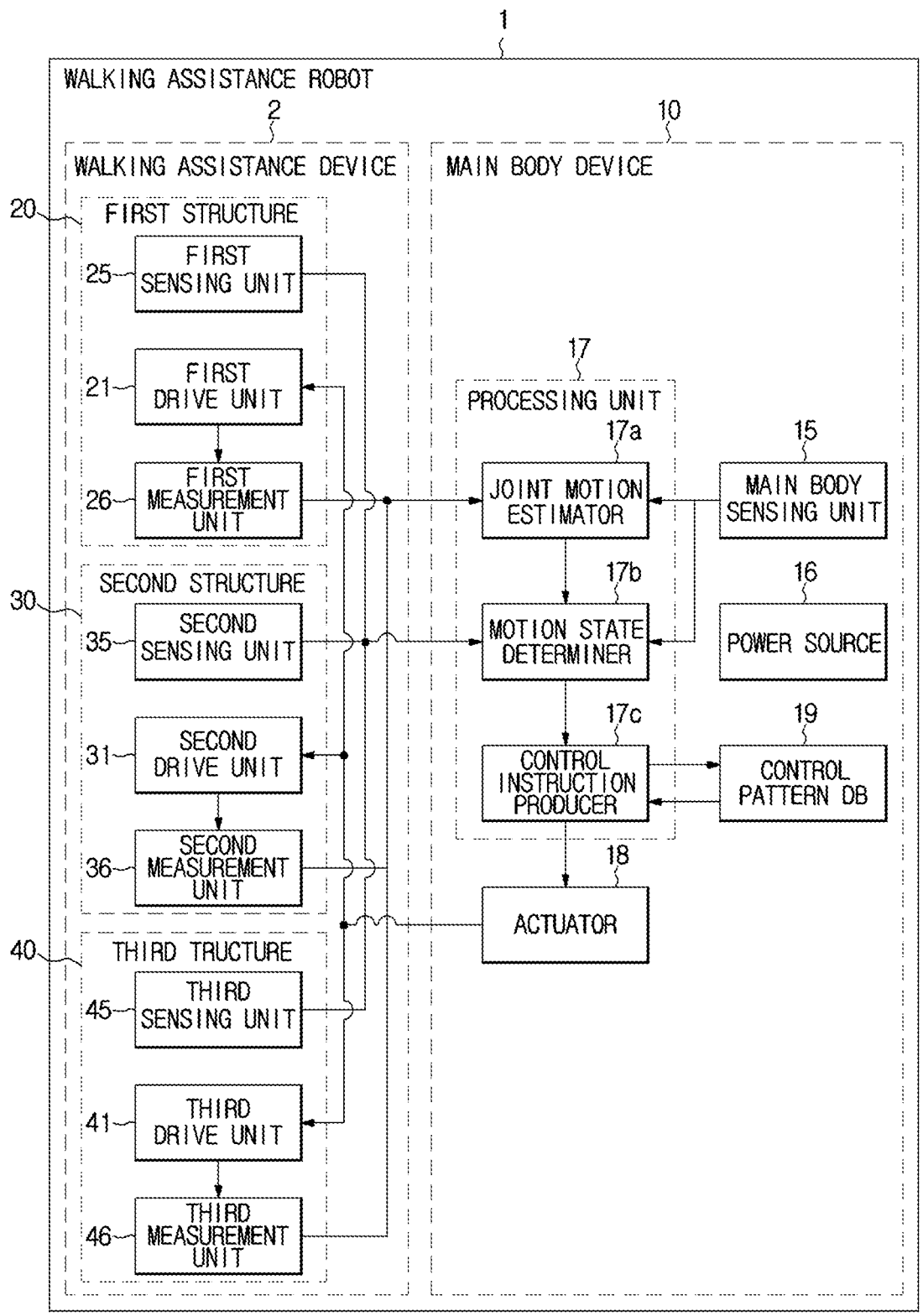
FIG. 3 is a view showing a configuration of one embodiment of a walking assistance robot.

FIGS. 1 and 2 are respectively a front view and a side view showing some example embodiment of a walking assistance robot, and FIG. 3 is a view showing a configuration of some example embodiment of a walking assistance robot.

As shown in FIGS. 1 to 3, the walking assistance robot 1 may include a walking assistance device 2 fixed to some or all of the wearer's legs or feet to assist a wearer in walking, and a main body device 10 to control the walking assistance device 2 and/or collect various information.

The walking assistance device 2, as shown in FIGS. 1 and 2, may include at least one of a first structure 20, a second structure 30, and a third structure 40. In the following description of the walking assistance robot 1, for clarity of explanation, example embodiments of the walking assistance robot 1 including all of the first structure 20, the second structure 30 and the third structure 40 will be described. However, the walking assistance robot 1 may not include all of the aforementioned first to third structures 20, 30 and 40, but may include only some of the first to third structures 20, 30 and 40, for example, the walking assistance robot 1 may include only the first structure 20.

According to some example embodiments, the walking assistance device 2 may include a single first structure 20, a single second structure 30, and a single third structure 40 such that one of the first to third structures 20, 30 and 40 may be worn by the wearer at any one of the left leg and the right leg. According to other example embodiments, as shown in FIG. 1, the walking assistance device 2 may be configured to be worn on both the left leg and the right leg of the wearer, and, therefore, the walking assistance device 2 may include a pair of first structures 20 and 20a, a pair of second structures 30 and 30a, and a pair of third structures 40 and 40a. In the case in which the walking assistance device 2 includes the pair of first structures 20 and 20a, the pair of second structures 30 and 30a, and the pair of third structures 40 and 40a, functions or operations of the pair of structures 20 and 20a, 30 and 30a or 40 and 40a may be substantially the same except for different driving directions. Likewise, according to other example embodiments, in the walking assistance device 2, some of the structures 20 to 40 may be provided in pairs. For example, the walking assistance device 2 may include a pair of first structures 20 and 20a, a single second structure 30, and a single third structure 40.

Hereinafter, example embodiments will be described with reference to the case in which single ones of the first to third structures 20 to 40 are provided, however, example embodiments are substantially equally applicable to the case in which each structure is provided in pairs.

The first structure 20 may assist movements of the wearer's upper leg and hip joint with regard to a walking motion. The first structure 20 may include at least one first drive unit 21 and at least one first support member 22.

The first drive unit 21 may generate various magnitudes of torque in response to a control instruction transmitted from a processing unit 17 of the main body device 10 or by driving of an actuator 18, and may apply the torque to the first support member 22. The first drive unit 21 may apply a fixed or variable torque to the first support member 22. The first drive unit 21 may rotate in at least one direction while applying the various magnitudes of torque to the first support member 22. A rotation range of the first drive unit 21 may be within a movement range of the wearer's hip joint.

According to some example embodiment, the first drive unit 21 may include at least one motor to generate the various magnitudes of torque using electric power fed from, e.g., a power source 16 of the main body device 10. The at least one motor may be a motor having an encoder. According to other example embodiments, the first drive unit 21 may include at least one piston or cylinder device which is operated by electric power, hydraulic pressure or pneumatic pressure fed from the main body device 10 to thereby generate torque. According to other example embodiments, the first drive unit 21 may include at least one motor as well as at least one piston or cylinder device.

The at least one first support member 22 may be connected to the first drive unit 21 and rotated in at least one direction using the torque generated by the first drive unit 21. The first support member 22 may have various shapes. For example, the first support member 22 may take the form of at least one support panel and/or include a plurality of knuckles and links connecting the knuckles to one another. The plurality of knuckles may take the form of support bars or support panels. At least one first fixing member 23 may be installed to the first support member 22. The first support member 22 may be fixed to the inner side or outer side of the wearer's upper leg by the first fixing member 23.

The first support member 22 may apply a desired magnitude of torque generated by the first drive unit 21 to the wearer's upper leg via the first fixing member 23. For example, when the first support member 22 is rotated by driving of the first drive unit 21, the wearer's upper leg, to which the first support member 22 is fixed via the first fixing member 23, may be rotated in the same direction. Consequently, the first structure 20 may apply the desired magnitude of torque to, e.g., the wearer's upper leg or hip joint to assist the wearer in raising or lowering the upper leg. In this way, the wearer may be assisted by the walking assistance robot 1 when raising their leg or during walking.

The first fixing member 23 may be formed of metal, or various other elastic materials, such as rubber, etc. The first fixing member 23 may take the form of a prescribed chain, an elastic band, or various other straps. Various other fixing members that may be employed by those skilled in the art to secure the first support member 22 to, e.g., the upper leg may also be applied to the first fixing member 23.

The first structure 20, as shown in FIG. 3, may further include at least one first sensing unit 25. The at least one first sensing unit 25 may sense at least one of operation of the first drive unit 21, operation of the first support member 22, and a motion of the wearer's hip joint. The first sensing unit 25 may produce an electrical signal based on the sensed result that includes information, such as, at least one of a joint angle, a gradient of the first support member 22, an angular velocity of a joint, and an acceleration of a joint. The first sensing unit 25 may transmit the information acquired thereby to a motion state determiner 17b.

The first sensing unit 25, for example, may include at least one of at least one joint angle sensor, at least one gradient sensor, at least one accelerometer, and at least one inertial measurement unit (IMU). The first sensing unit 25 may be installed to at least one of the first drive unit 21 and the first support member 22. For example, the first sensing unit 25 may be installed to both the first drive unit 21 and the first support member 22. In addition, some components of the first sensing unit 25 may be installed to the first drive unit 21 and the other components of the first sensing unit 25 may be installed to the first support member 22. For example, the joint angle sensor may be installed to the first drive unit 21, and the gradient sensor or the inertial measurement unit may be installed to the first support member 22.

As illustrated in FIG. 3, according to some example embodiments, the first structure 20 may also include at least one first measurement unit 26. The at least one first measurement unit 26 may be connected to the first drive unit 21 to measure information related to operation of the first drive unit 21. The information related to operation of the first drive unit 21 may include at least one of a rotation angle, angular velocity, and angular acceleration of the first drive unit 21. For example, if the first drive unit 21 includes a motor having an encoder, the first measurement unit 26 may measure a joint angle, velocity, and acceleration using an encoder value of the encoder. The first measurement unit 26 may transmit various parameters measured thereby to a joint motion estimator 17a.

The second structure 30 may assist movements of the wearer's lower leg and knee joint with regard to a walking motion. The second structure 30 may include a second drive unit 31, a second support member 32, and a second fixing member 33.

The second drive unit 31 may generate various magnitudes of torque in at least one direction, in the same manner as the first drive unit 21. Similarly, the second drive unit 31 may include at least one motor and/or at least one piston or cylinder device. The at least one motor of the second drive unit 31 may have an encoder.

The at least one second support member 32 may be rotated in at least one direction using torque generated by the second drive unit 31. A configuration, structure, material and the like of the second support member 32 may be equal to or different from those of the above-described first support member 22.

The second structure 30 may include one or more second fixing members 33 and 34 to secure the second support member 32 to the wearer's lower leg. The second support member 32 may be fixed to the inner side or outer side of the wearer's lower leg by the second fixing members 33 and 34. A configuration, structure, material and the like of the second fixing members 33 and 34 may be equal to or different from those of the above-described first fixing member 23. As the second support member 32 may be fixed to the lower leg by the second fixing members 33 and 34, the second structure 30 may apply a prescribed magnitude of torque to, e.g., the wearer's lower leg or knee joint. In this way, the second structure 30 may assist the wearer in raising or lowering the lower leg.

As shown in FIG. 3, the second structure 30 may include at least one second sensing unit 35. The at least one second sensing unit 35 may sense at least one of operation of the second drive unit 31, operation of the second support member 32, and a motion of the wearer's knee joint, may convert the sensed result into an electrical signal, and may transmit the electrical signal to the motion state determiner 17b. The second sensing unit 35 may include at least one of at least one joint angle sensor, at least one gradient sensor, at least one accelerometer, and at least one inertial measurement unit. The second sensing unit 35 may be installed to at least one of the second drive unit 31 and the second support member 32. In the same manner as the first sensing unit 25, some components of the second sensing unit 35 may be installed to the second drive unit 31 and other components may be installed to the second support member 32.

As shown in FIG. 3, according to some example embodiments, the second structure 30 may include at least one second measurement unit 36. The at least one second measurement unit 36 may measure information related to operation of the second drive unit 31, for example, a rotation angle, angular velocity, and angular acceleration of the second drive unit 31. If the second drive unit 31 includes a motor having an encoder, the second measurement unit 36 may measure a joint angle, velocity, and acceleration using an encoder value of the encoder. The second measurement unit 36 may transmit various parameters collected thereby to the joint motion estimator 17a.

The third structure 40 may assist a motion of the wearer's ankle with regard to a walking motion. The third structure 40 may include a third drive unit 41, a footrest member 42, and a third fixing member 43.

In the same manner as the first drive unit 21, the third drive unit 41 may generate various magnitudes of torque in at least one direction to assist a motion of the wearer related to an ankle joint and muscles around the ankle. The third drive unit 41 may include at least one of at least one motor and at least one piston or cylinder device, in the same manner as the first drive unit 21 and the second drive unit 31. The at least one motor may have an encoder.

The footrest member 42 may be configured to support the wearer's sole seated thereon.

The third fixing member 43 may serve to fix the wearer's foot seated on the footrest member 42 to the footrest member 42. A configuration, structure, material and the like of the third fixing member 43 may be equal to or different from those of the above-described first fixing member 23 or the second fixing member 33 or 34.

As shown in FIG. 3, the third structure 40 may further include at least one third sensing unit 45. The at least one third sensing unit 45 may sense at least one of operation of the third drive unit 41, operation of the third fixing member 43, and a motion of the wearer's ankle joint. The third sensing unit 45 may include at least one of at least one joint angle sensor, at least one gradient sensor, at least one accelerometer, and at least one inertial measurement unit. The third sensing unit 45 may also include a pressure sensor. The pressure sensor may be installed to the footrest member 42. The pressure sensor may sense, based on the sensed wearer's weight, whether or not the wearer is wearing the walking assistance robot 1 and/or may sense whether or not the wearer is standing. In addition, the pressure sensor may be a ground reaction force (GRF) sensor to sense ground reaction force transmitted to the wearer's foot during walking. The third sensing unit 45 may transmit a signal produced thereby based on the aforementioned sensing to the motion state determiner 17b.

As shown in FIG. 3, the third structure 40 may also include at least one third measurement unit 46. The at least one third measurement unit 46 may measure information related to operation of the third drive unit 41 and transmit the measured information to the joint motion estimator 17a. If the third drive unit 41 includes a motor having an encoder, the third measurement unit 46 may measure a joint angle, velocity, and acceleration using an encoder value of the encoder.

According to some example embodiments, the number of the first to third fixing members 23, 33, 34 and 43 of the walking assistance robot 1 may be greater or less than the above description of the walking assistance robot 1.

Operation of the above-described first to third structures 20 to 40 may be initiated or controlled by the actuator 18 installed to the main body device 10. The first to third structures 20 to 40 may receive control signals individually, or may be operated by the actuator 18 upon receiving power.

The main body device 10 may control operation of the walking assistance device 2 and/or collect various information. In addition, the main body device 10 may support the wearer's upper body to assist the wearer in stably wearing the walking assistance robot 1.

As shown in FIGS. 1 and 2, the main body device 10 may include a housing 10a in which a variety of elements to control the walking assistance robot 1 may be accommodated. The housing 10a may accommodate, for example, a main body sensing unit 15, the power source 16, and a printed circuit board on which a processor or various semiconductor chips to implement functions of the processing unit 17 may be mounted. The housing 10a of the main body device 10 may safely protect or stably fix the various elements accommodated in the housing 10a. The housing 10a may accommodate various elements to control the walking assistance robot 1, such as, e.g., the printed circuit board on which the processor or various semiconductor chips to provide functions of the processing unit 17 may be mounted.

The main body device 10 may further include one or more first and second waist fixing members 11 and 12. The first and second waist fixing members 11 and 12 may serve to fix the housing 10a to a part of the wearer's body, e.g., to the wearer's waist. For example, the first waist fixing member 11 may be connected to the housing 10a, and the second waist fixing member 12 may be connected to a first waist support member 13. The first and second waist fixing members 11 and 12 may be formed of metal or various elastic materials, such as rubber, etc., and may take the form of chains, elastic bands, or various other straps. Various other fixing members that may be employed by those skilled in the art to fix the housing 10a to the waist, hips or the like may be used as the first and second waist fixing members 11 and 12. The main body device 10 may further include the first waist support member 13 to support the wearer's waist. The first waist support member 13 may be designed to have a shape corresponding to the shape of the wearer's waist in order to support the wearer's waist. The first waist support member 13 may be connected to the housing 10a by at least one second waist support member 14.

As shown in FIG. 3, the main body device 10 may include the main body sensing unit 15, the power source 16, the processing unit 17, and the actuator 18, for example.

The main body sensing unit 15 may sense various motions of the wearer and/or collect various information related to the motions. For example, the main body sensing unit 15 may sense a walking speed of the wearer. The main body sensing unit 15 may include at least one of at least one velocity sensor, at least one gradient sensor, at least one accelerometer, at least one inertial measurement unit, and a position measurement unit, such as, e.g., a global positioning system (GPS) unit.

The power source 16 may supply power to the various elements inside the housing 10a or elements of the respective drive units 21, 31 and 41 of the walking assistance device 2. The power source 16 may be accommodated in the housing 10a. The power source 16 may be a primary cell or a secondary cell. The primary cell may include at least one of a mercury cell, a manganese cell, an alkaline cell, and a lithium cell. The secondary cell may include a nickel-cadmium (Ni—cd) cell, a nickel-hydrogen (Ni-MH) cell, a lead-acid cell, a lithium-ion (Li-ion) cell, a lithium-polymer cell, etc.

The processing unit 17 may determine a motion state of at least one joint, such as, e.g., a hip joint, a knee joint, and an ankle joint, or an operational state of the drive unit 21, 31 or 41 corresponding to each joint based on information transmitted from the first to the third sensing units 25, 35 and 45 and/or the first to third measurement units 26, 36 and 46. In addition, the processing unit 17 may produce a control signal to control the walking assistance robot 1 based on the determined result with regard to the motion state of the at least one joint or the operational state of the drive unit 21, 31 or 41 corresponding to each joint.

The processing unit 17 may include a processor accommodated in the housing 10a. The processor may be a processing device in which an arithmetic logic unit, register, program counter, instruction decoder, control circuit, or the like is mounted on at least one silicon chip. The processor may be embodied by at least one semiconductor chip mounted on the printed circuit board accommodated in the housing 10a.

In more detail, the processing unit 17 may include a processor and a memory (not shown).

Figure 8:
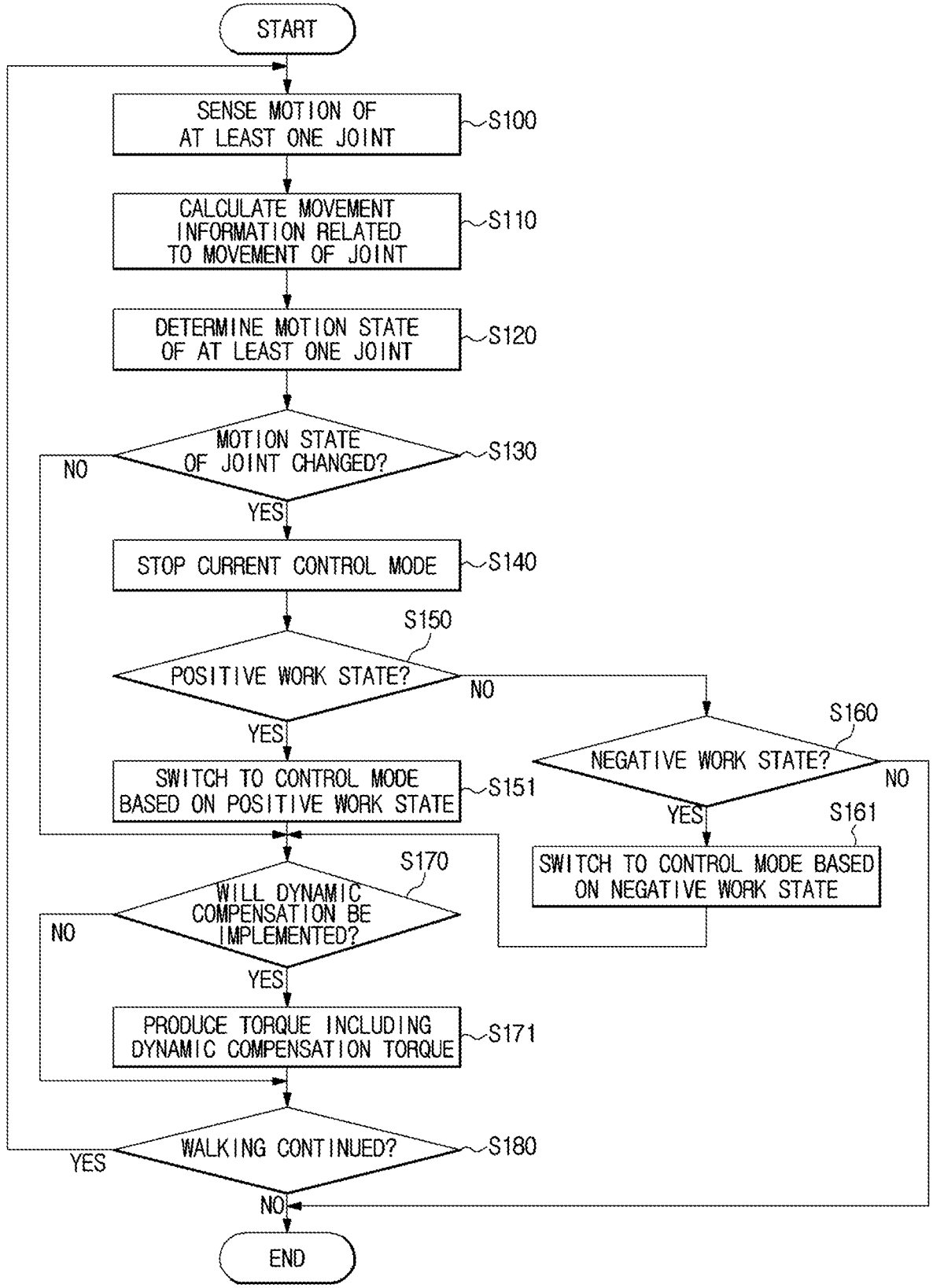
FIG. 8 is a flowchart showing one embodiment of a method of controlling a walking assistance robot.

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processing device as a special purpose computer to perform the operations illustrated in FIGS. 8 and/or 9, such that the processing unit 17 controls the actuator 18 and/or the drive units 21, 31 and 41 of the walking assistance device 2 based on signals indicating the motion state of the at least one joint or the operational state of the drive units 21, 31 and 41.

The instructions may be stored on a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion. The program instructions may be executed by one or more processors.

As shown in FIG. 3, the processing unit 17 may include the joint motion estimator 17a, the motion state determiner 17b, and a control instruction producer 17c.

The joint motion estimator 17a may estimate motion of a joint by calculating inverse dynamic models of the wearer and the walking assistance robot 1 based on at least one piece of information related to motions transmitted from the respective measurement units 26, 36 and 46. For example, in some example embodiments, the joint motion estimator 17a may estimate the motion of a joint based on a walking model.

Figure 4:
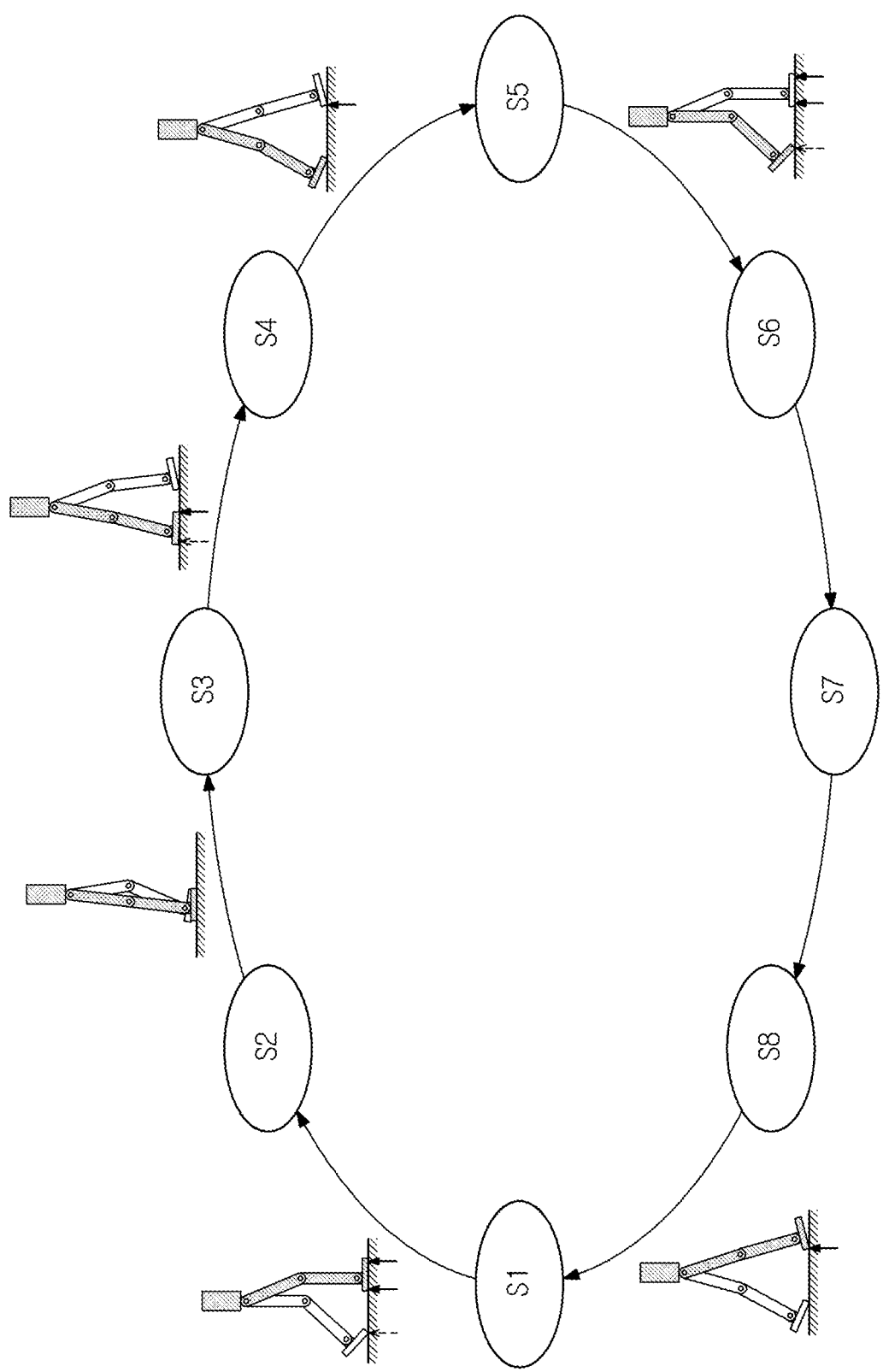
FIGS. 4 and 5 are explanatory views of one embodiment of a walking model.
Figure 5:
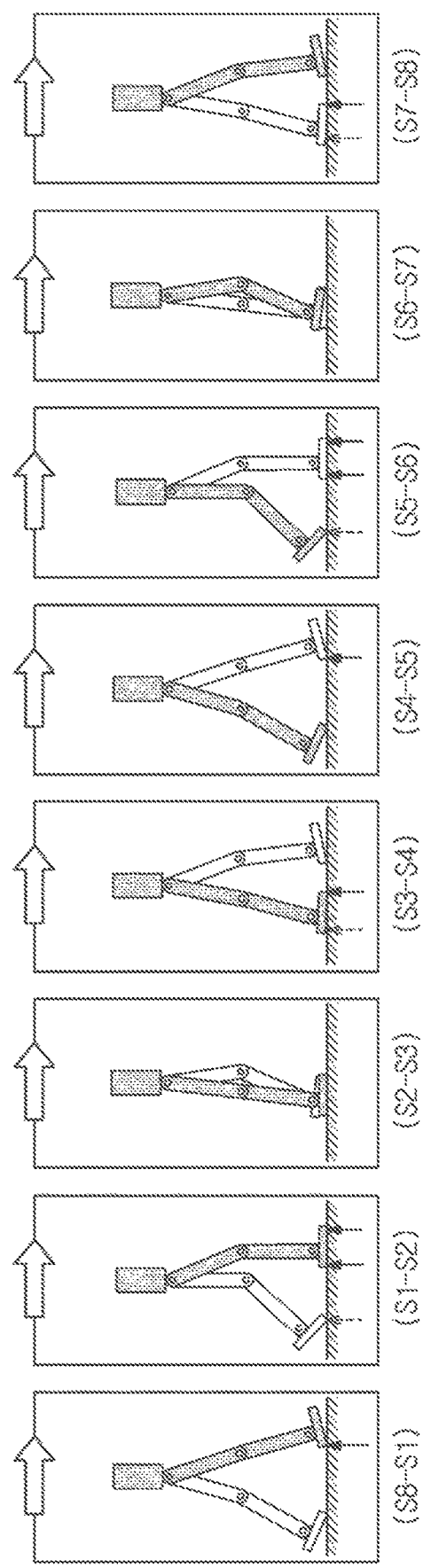

FIGS. 4 and 5 are explanatory views of a finite state machine mode according to some example embodiments of a walking model.

Referring to FIG. 4, a walking operation of the wearer may be divided into eight phases s1 to s8.

In a first walking phase s1, the right leg may be in a loading response (LR) state and the left leg may be in a pre-swing (PSw) state. The heel of the right foot may touch a ground during phase transition from an eighth walking phase s8 to the first walking phase s1 as shown in FIGS. 4 and 5. On the other hand, the toes of the left foot may be in contact with the ground, and the heel of the left foot may be separated from the ground during the aforementioned phase transition (s8-s1).

In a second walking phase s2, the right leg is in a mid-stance (MSt) state and the left leg is in an initial swing (ISw) state. Both the heel and toes of the right foot may be in contact with the ground and the left leg initiates a swing motion during phase transition from the first walking phase s1 to the second walking phase s2. The heel of the left foot may first leave the ground and the toes of the left foot may leave the ground after the heel of the left foot is separated from the ground during the aforementioned phase transition (s1-s2).

In a third walking phase s3, the right leg is still in the mid-stance (MSt) state and the left leg is in a mid-swing (MSw) state. Both the heel and toes of the right foot are in contact with the ground and the left leg continuously implements the swing motion during phase transition from the second walking phase s2 to the third walking phase s3. The right foot and the left foot may be located proximate to each other during the aforementioned phase transition (s2-s3).

In a fourth walking phase s4, the right leg is in a terminal stance (TSt) state and the left leg is in a terminal swing (TSw) state. The heel of the right foot begins to leave the ground during phase transition from the third walking phase s3 to the fourth walking phase s4. On the other hand, the toes of the right foot may be in contact with the ground yet. Meanwhile, the left foot does not touch the ground yet during the aforementioned phase transition (s3-s4).

In a fifth walking phase s5, the left leg is in the loading response (LR) state and the right leg corresponds to the pre-swing (PSw) state. The heel of the left foot touches the ground during phase transition from the fourth walking phase s4 to the fifth walking phase s5. Meanwhile, the toes of the right foot may still be in contact with the ground, and the heel of the right foot may be separated from the ground during the aforementioned phase transition (s4-s5).

In a sixth walking phase s6, the left leg is in the mid-stance (MSt) state and the right leg corresponds to the initial swing (ISw) state. The heel and toes of the left foot may touch the ground during phase transition from the fifth walking phase s5 to the sixth walking phase s6. The right left may initiate a swing motion as the toes of the right foot leave the ground during the aforementioned phase transition (s5-s6).

In a seventh walking phase s7, the left leg is still in the mid-stance (MSt) state and the right leg corresponds to the mid-swing (MSw) state. Both the heel and toes of the left foot are in contact with the ground during phase transition from the sixth walking phase s6 to the seventh walking phase s7, and the right leg continuously implements the swing motion during the aforementioned phase transition (s6-s7).

In the eighth walking phase s8, the left leg is in the terminal-stance (TSt) state and the right leg corresponds to the terminal swing (TSw) state. The right foot does not touch the ground yet and the heel of the left foot begins to leave the ground during phase transition from the seventh walking phase s7 to the eighth walking phase s8 during the aforementioned phase transition (s7-s8).

The above-described first to eighth phases s1 to s8 may be successively repeated during walking.

The at least one measurement unit 26, 36 or 46 may measure and collect information related to motion of at least one joint during the phase transitions s8-s1 to s7-s8 during walking. The at least one measurement unit 26, 36 or 46 may measure information related to the motion of the joint at any one specific point in time during the phase transitions s8-s1 to s7-s8. According to example embodiments, the at least one measurement unit 26, 36 or 46 may measure information related to the motion of the joint at plural specific points of time during one phase transition, and acquire an average or intermediate value of plural specific pieces of information.

For example, the at least one measurement unit 26, 36 or 46 may collect information related to motion of at least one joint corresponding to the at least one measurement unit 26, 36 or 46 among a plurality of joints of the wearer. In addition, the at least one measurement unit 26, 36 or 46 may collect information related to operation of at least one drive unit 21, 31 or 41 corresponding to the at least one measurement unit 26, 36 or 46 among the first to third drive units 21, 31, and 41, thereby collecting information related to motion of at least one joint. In this case, the information measured by the at least one measurement unit 26, 36 or 46 may include at least one of an angle of at least one joint, an angular velocity of at least one joint, an angular acceleration of at least one joint, a walking speed of the walking assistance robot 1, and ground reaction force. The information measured by the at least one measurement unit 26, 36 or 46 may be transmitted to the joint motion estimator 17a, or may be temporarily or permanently stored in a storage device, and, thereafter transmitted to the joint motion estimator 17a.

According to some example embodiment, the at least one measurement unit 26, 36 or 46 may measure and collect information related to motion of at least one joint during all phase transitions. According to other example embodiments, the at least one measurement unit 26, 36 or 46 may collect information related to motion of at least one joint only during some phase transitions. For example, the at least one measurement unit 26, 36 or 46 may measure and collect information related to motion of at least one joint only during the first phase transition s8-s1 to the fourth phase transition s3-s4.

According to some example embodiment, when the at least one measurement unit 26, 36 or 46 measures and collects information related to motion of at least one joint, time information regarding a measurement point in time may also be transmitted, along with other information, to the joint motion estimator 17a.

The joint motion estimator 17a may calculate and estimate motion of a joint using time information regarding a point in time when the measurement unit 26, 36 or 46 implements measurement as well as information measured by the measurement unit 26, 36 or 46. In this case, the estimated motion of the joint may be used to determine a motion state of at least one joint in subsequent walking phases. For example, the estimated motion of the joint during the first phase transition s8-s1 to the fourth phase transition s3-s4 may be used to determine a motion state of at least one joint during the fifth walking phase s5 to the eighth walking phase s8.

The joint motion estimator 17a may estimate information related to motion of a joint between plural points in time when information related to the motion of the joint is measured using interpolation. For example, the joint motion estimator 17a may estimate an angle, angular velocity, and angular acceleration of the joint.

The joint motion estimator 17a may calculate torque of at least one joint based on at least one measured value from at least one of the first to third measurement units 26, 36 and 46. The joint motion estimator 17a may utilize various parameters related to motion of at least one joint measured by the first to third measurement units 26, 36 and 46, e.g., an angle, angular velocity, and acceleration of the joint to calculate the torque of the at least one joint.

According to some example embodiment, the joint motion estimator 17a may calculate torque of a joint using the following Equation 1.

$$\tau = M(q)\frac{d^2q}{dt^2} + C\left(q, \frac{dq}{dt}\right) + G(q) \quad \text{Equation 1}$$

In Equation 1, τ is torque of the joint, q is an angle of the joint, and t is time. Thus, dq/dt is an angular velocity of the joint, and d²q/dt² is an angular acceleration of the joint. M(•) is a function for reflection of a mass that is variable based on the wearer's pose, and C(•) is a function for reflection of Coriolis force depending on rotation of a leg, and G(•) is a function for reflection of gravity. According to some example embodiments, the respective functions may be defined by the user, or may be selected by the user from among plural predefined functions.

The joint motion estimator 17a may transmit at least one estimated or calculated result generated by the joint motion estimator 17a, e.g., the estimated or calculated result of the torque, angle, angular velocity, or angular acceleration of the joint to the motion state determiner 17b.

The motion state determiner 17b may determine whether motion of at least one joint is in a positive work state or a negative work state based on the sensed or measured motion of the joint.

According to some example embodiments, the motion state determiner 17b may determine a motion state using a signal transmitted from at least one of the first to third sensing units 25, 35 and 45. According to other example embodiments, the motion state determiner 17b may receive information related to the estimated motion of the joint from the joint motion estimator 17a, e.g., data regarding an estimated torque or angle value of the joint, and determine a motion state of the joint based on the received data.

According to some example embodiments, the motion state determiner 17b may calculate movement information (e.g. power and/or work) related to movement of at least one joint based on the sensed or measured motion of the joint. For example, the motion state determiner 17b may calculate movement information related to movement of the joint based on torque sensed by the first to third sensing units 25, 35 and 45 or torque of the joint estimated by the joint motion estimator 17a. According to some example embodiments, the motion state determiner 17b may calculate movement information, e.g., power using the following Equation 2.

$$P = \tau(t)\frac{dq}{dt} \quad \text{Equation 2}$$

In Equation 2, P is power, τ(t) is a function of torque based on time, q(t) is an angle of the joint based on time, and dq/dt is an angular velocity of the joint based on time. The motion state determiner 17b may include power P in the movement information using Equation 2.

Power is the rate of performing Work, therefore, the motion state determiner 17b may calculate Work W by the following Equation 3 via the integral of power P represented by Equation 2.

$$W = \int_{t1}^{t2} \tau(t)\frac{dq}{dt}dt \quad \text{Equation 3}$$

In Equation 3, W is work, like power P, work W may be utilized as the movement information.

The motion state determiner 17b may determine that a motion state of a joint is a positive work state if the calculated movement information, i.e. power P or work W, has a positive value or is changed to a positive value. If the calculated movement information has a negative value or is changed to a negative value, the motion state determiner 17b may determine that a motion state of a joint is a negative work state.

In addition, the motion state determiner 17b may determine, based on the sensed or measured motion of at least one joint, whether or not a motion state of the joint is changed. For example, the motion state determiner 17b may determine whether a motion state of the joint is changed from a stationary state to a positive work state or a negative work state. In addition, the motion state determiner 17b may determine whether a motion state of the joint is changed from a positive work state or a negative work state to a negative work state or a positive work state.

The motion state determiner 17b may determine a motion state on a per joint basis or on a per drive unit 21, 31 or 41 basis.

The control instruction producer 17c may produce a control instruction based on the determined result from the motion state determiner 17b, and thereafter transmit the control instruction to the actuator 18 or the respective drive units 21, 31 and 41, thereby controlling motion of the walking assistance robot 1.

The control instruction producer 17c may stop a current control mode and initiate a new control mode if the motion state determiner 17b transmits the determined result representing that a motion state of a joint is changed. If the motion state determiner 17b transmits the determined result representing that a motion state of a joint is not changed, the control instruction producer 17c may maintain a current control mode without stop.

If the motion state determiner 17b transmits the determined result representing that a joint is in a positive work state, the control instruction producer 17c may control the walking assistance robot 1 based on an acceleration assistance control mode to accelerate motion of at least one joint. If the motion state determiner 17b transmits the determined result representing that a joint is in a negative work state, the control instruction producer 17c may control the walking assistance robot 1 based on a deceleration assistance control mode to decelerate motion of at least one joint.

The control instruction producer 17c may acquire a control pattern based on each state via reading a control pattern from a control pattern database 19, and thereafter produce a control signal based on the acquired control pattern. The produced control signal may be transmitted to the actuator 18 or the walking assistance device 2.

The control instruction produced by the control instruction producer 17c may be adjusted to apply dynamic compensation torque for compensation of external force, such as gravity, ground reaction force, etc. to the at least one joint, and thereafter transmit the control instruction to the respective drive units 21, 31 and 41.

According to some example embodiment, the control instruction producer 17c may calculate torque to be applied to at least one joint based on the following Equation 4, produce a control instruction for the actuator 18 or the walking assistance device 2 based on the calculated torque, and thereafter transmit the produced control signal to the actuator 18 or the walking assistance device 2.

$$\tau_{des} = W_{sync}(\tau_{pw} + \tau_{nw}) + \tau_{comp} \qquad \text{Equation 4}$$

In Equation 4, $\tau_{des}$ is assistance torque to be applied to a joint, $\tau_{pw}$ is active torque, $\tau_{nw}$ is damping torque, $W_{sync}$ is a human and robot synchronization index to represent the synchronization level of the wearer and the walking assistance robot 1, and $\tau_{comp}$ is dynamic compensation torque.

Hereinafter, the active torque $\tau_{pw}$ of Equation 4 will be described.

Active torque $\tau_{pw}$ is torque to be applied to the wearer's leg to assist acceleration of the wearer's leg. According to some example embodiments, active torque $\tau_{pw}$ may be decided as represented by the following Equation 5 and Equation 6.

$$\tau_{pw} = A(t) \cdot \text{sign}\left(\frac{dq}{dt}\right) - D_n, \text{ if active.} \qquad \text{Equation 5}$$

$$\tau_{pw} = 0, \text{ if deactive} \qquad \text{Equation 6}$$

Equation 5 is an equation to calculate active torque $\tau_{pw}$ under activation of active torque $\tau_{pw}$, and Equation 6 is an equation to calculate active torque $\tau_{pw}$ under deactivation of active torque $\tau_{pw}$.

In Equations 5 and 6, A(t) is a function representing a torque variation pattern that shows variation of torque based on time t, sign(•) is a function to decide the sign of the torque variation pattern. Thus, sign(•) may output 1 if an input value is a positive number, and the function sign(•) may output −1 if an input value is a negative number. $D_n$ is a negative damping coefficient for reflection of negative damping, and may be less than zero.

Figure 6:
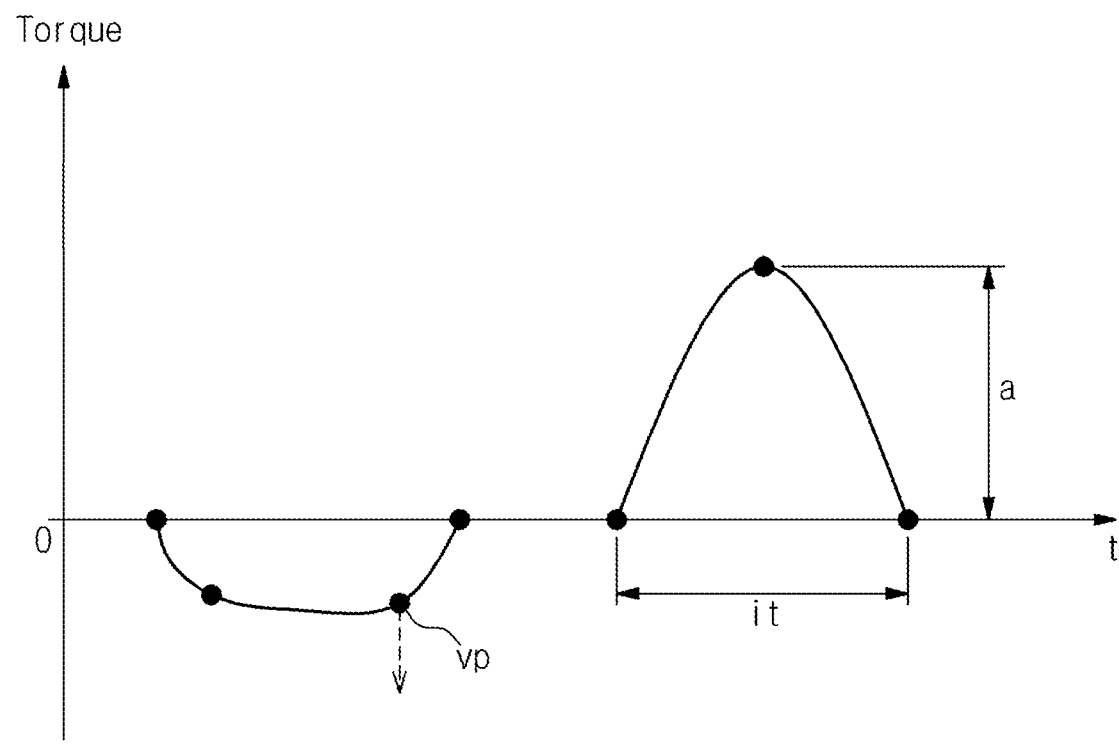
FIG. 6 is an explanatory view of one embodiment of a torque variation pattern.

FIG. 6 is an explanatory view of some example embodiments of a function representing a torque variation pattern A(t) of Equation 5.

Referring to FIG. 6, in some example embodiment, the torque variation pattern A(t) may be acquired based on time information t regarding time upon change of a previous walking state, torque variation position information vp regarding a torque variation position, and information regarding maximum joint torque in a current walking state.

The time information t regarding time upon change of a previous walking state may be acquired using time information regarding a measurement point in time acquired from a finite state machine model upon state change.

The torque variation position information vp regarding a torque variation position may be acquired using information regarding a joint angle upon state change as well as the information regarding a measurement point in time acquired from a finite state machine model. For example, since a torque direction may be changed if the joint angle becomes the maximum, the torque variation position information vp regarding a torque variation position may be acquired using time information regarding a point in time when the joint angle becomes the maximum.

Based on the time information t regarding time upon change of a previous walking state and the information vp regarding a torque variation position, a period it during which a torque direction is constant may be acquired. Meanwhile, a magnitude of torque to be applied may be proportional to the maximum joint torque in a current walking state. In this case, the magnitude of torque to be applied may be defined as a value less than the maximum joint torque. Through acquisition of the time information t regarding time upon change of a previous walking state, the torque variation position information vp regarding a torque variation position, the period during which a torque direction is constant, the information regarding the maximum joint torque in a current walking state as described above, as shown in FIG. 6, the function of a torque variation pattern A(t) based on time t may be defined.

The negative damping coefficient $D_n$ of Equation 5 is a value to assist acceleration of motion of a joint by applying vibration to the joint.

When using active torque $\tau_{pw}$, the control instruction producer 17c may calculate active torque $\tau_{pw}$ using Equation 5, and, thereafter calculate the assistance torque $\tau_{des}$ using the calculated active torque $\tau_{pw}$. The assistance torque $\tau_{des}$ including active torque $\tau_{pw}$ may be applied to a joint. If damping torque $\tau_{nw}$ is zero, assistance torque $\tau_{des}$ of Equation 4 may be acquired using only active torque $\tau_{pw}$ and dynamic compensation torque $\tau_{comp}$.

When not using active torque $\tau_{pw}$, the active torque $\tau_{pw}$ may be zero as represented by Equation 6. As active torque $\tau_{pw}$ is zero, only damping torque $\tau_{nw}$ and dynamic compensation torque $\tau_{comp}$ remain in Equation 4. Consequently, the control instruction producer 17c may calculate the assistance torque $\tau_{des}$ including only damping torque $\tau_{nw}$ and dynamic compensation torque $\tau_{comp}$ and apply the calculated assistance torque $\tau_{des}$ to a joint.

If a motion state of a joint is a positive work state, the control instruction producer 17c may acquire assistance torque $\tau_{des}$ including active torque $\tau_{pw}$ by calculating active torque $\tau_{pw}$ using Equation 5, and thereafter produce a control signal for the respective drive units 21, 31 and 41 based on the assistance torque $\tau_{des}$ and transmit the control signal to the respective drive units 21, 31 and 41. If a motion state of a joint is not a positive work state, the control instruction producer 17c may decide that active torque $\tau_{pw}$ is zero as represented by Equation 6 and thus acquire assistance torque $\tau_{des}$ not including active torque $\tau_{pw}$. The case in which a motion state of a joint is not a positive work state, for example, may be the case in which a motion state of a joint is a negative work state.

Hereinafter, damping torque $\tau_{nw}$ of Equation 4 will be described.

According to some example embodiments, the control instruction producer 17c may calculate the damping torque $\tau_{nw}$ using the following Equation 7 and Equation 8.

$$\tau_{nw} = -D_p \frac{dq}{dt}, \text{if activation} \quad \text{Equation 7}$$

$$\tau_{nw} = 0, \text{if deactivation} \quad \text{Equation 8}$$

Equation 7 is an equation to calculate damping torque $\tau_{nw}$ under activation of damping torque $\tau_{nw}$, and Equation 8 is an equation to calculate damping torque $\tau_{nw}$ under deactivation of damping torque $\tau_{nw}$.

In Equation 7, $D_p$ is a positive damping coefficient that may be randomly selected. With reference to description of Equation 7, a magnitude of damping torque $\tau_{nw}$ may be proportional to an angular velocity dq/dt of a joint and a direction of damping torquer nw may be opposite to a direction of the angular velocity dq/dt of the joint.

By determining the damping torque $\tau_{nw}$ based on the angular velocity dq/dt of the joint, the walking assistance device 2 may prevent a walking speed from decreasing beyond expectation, which makes it unnecessary to apply high assistance torque during following walking phases. In this way, the walking assistance robot 1 may more effectively implement walking.

As discussed supra, the control instruction producer 17c may calculate the assistance torque $\tau_{des}$ using Equation 4 based on the active torque $\tau_{pw}$, the damping torque $\tau_{nw}$ and the dynamic compensation torque $\tau_{comp}$. When using the damping torque $\tau_{nw}$, the damping torque $\tau_{nw}$ may have a non-zero value calculated based on Equation 7. In this case, the assistance torque $\tau_{des}$ including a non-zero damping torque $\tau_{nw}$ may be calculated by the control instruction producer 17c using Equation 4 and applied to a joint. If active torque $\tau_{pw}$ is zero, assistance torque $\tau_{des}$ may be acquired using only damping torque $\tau_{nw}$ and dynamic compensation torque $\tau_{comp}$. Assuming the case of not using damping torque $\tau_{nw}$, damping torque $\tau_{nw}$ may be zero as represented by Equation 8, and thus only active torque $\tau_{pw}$ and dynamic compensation torque $\tau_{comp}$ remain in Equation 4. Consequently, assistance torque $\tau_{des}$ including only active torque $\tau_{pw}$ and dynamic compensation torque $\tau_{comp}$ may be applied to a joint.

If a motion state of a joint is a negative work state, the control instruction producer 17c may acquire assistance torque $\tau_{des}$ including damping torque $\tau_{nw}$ by calculating damping torque $\tau_{pw}$ based on Equation 7, and thereafter produce a prescribed control signal for the respective drive units 21, 31 and 41 based on the assistance torque $\tau_{des}$. Then, the control instruction producer 17c may transmit the produced control signal to the respective drive units 21, 31 and 41. If a motion state of a joint is not a negative work state, e.g., if a motion state of a joint is a positive work state, the control instruction producer 17c may decide that damping torque $\tau_{nw}$ is zero as represented by Equation 6 and thus acquire assistance torque $\tau_{des}$ not including damping torque $\tau_{nw}$.

Hereinafter, the synchronization index $W_{sync}$ of Equation 4 will be described.

The synchronization index $W_{sync}$ may represent similarity between the wearer and the walking assistance robot 1. Such similarity may be acquired via comparison of repeatability or periodicity of walking phases. By factoring the synchronization index $W_{sync}$ in torque to be applied to a joint, the walking assistance robot 1 may apply a more active assistance torque and, therefore, the walking assistance robot 1 may prevent incorrect assistance torque from being applied to each joint.

According to some example embodiments, the synchronization index $W_{sync}$ may be calculated by the following Equation 9.

$$w_{sync} = \frac{1}{w_1 \| P_{k-1} - P_k \|^2 + w_2 \| t_{k-1} - t_k \|^2} \quad \text{Equation 9}$$

In Equation 9, $w_1$ and $w_2$ are weighting values that may be selected by system designers, etc., P is information regarding motion during phase transition, t is information regarding phase transition time, k is an index representing a current state, and k−1 is an index representing a previous state. Thus, $P_k$ is information regarding motion during current phase transition, and $P_{k-1}$ is information regarding motion during previous phase transition.

Hereinafter, the dynamic compensation torque $\tau_{comp}$ of Equation 4 will be described.

The walking assistance robot 1 may factor the dynamic compensation torque $\tau_{comp}$ into the assistance torque $\tau_{des}$ to reduce resistance of the wearer against the walking assistance robot 1 due to friction or energy loss of various elements of the walking assistance robot 1, gravity or ground reaction force, etc. The dynamic compensation torque $\tau_{comp}$ may be applied, along with active torque $\tau_{pw}$ or damping torque $\tau_{nw}$, to a joint. In addition, the dynamic compensation torque $\tau_{comp}$ may be applied to a joint even when active torque $\tau_{pw}$ or damping torque $\tau_{nw}$ is not applied to the joint.

According to some example embodiments, the dynamic compensation torque $\tau_{comp}$ may be equally or differently applied to the leg when the leg is in a stance (St) state and when the leg in a swing (Sw) state.

According to one embodiment, dynamic compensation torque $\tau_{comp}$ applied to a joint of the leg in a stance state (St) may be calculated by the following Equation 10.

$$\tau_{comp} = K_s(q_d - q) + D_v \frac{dq}{dt} + G(q) \quad \text{Equation 10}$$

In Equation 10, $K_s(\bullet)$ is a function defined for compensation of strength, $D_v(\bullet)$ is a function defined for compensation of viscous friction, and $G(\bullet)$ is a function defined for compensation of gravity. $q_d$ is an angle of a joint in an ideal state, and q is a measured angle of the joint. dq/dt is an angular velocity of the joint.

In other words, if the leg is in the stance state (St), dynamic compensation torque $\tau_{comp}$ may further be applied to a joint of the leg, to enable compensation of strength, viscous friction, and gravity.

According to some example embodiment, the dynamic compensation torque $\tau_{comp}$ applied to a joint of the leg in the swing state (Sw) may be calculated using the above Equation 10 and, as discussed in more detail below, may also utilize the following Equation 11 and Equation 12 to calculate the dynamic compensation torque$\tau_{comp}$ depending on the speed of the swing.

When the leg swings at a low speed, dynamic compensation torque $\tau_{comp}$ may be calculated by the above Equation 10, in the same manner as that when the leg is in a stance state.

When the leg swings at a high speed, dynamic compensation torque $\tau_{comp}$ may be calculated by the following Equation 11 and Equation 12.

$$\tau_{comp} = K_s(q_d - q) + D_v \frac{dq}{dt} + M(q)\frac{d^2q}{dt^2} \quad \text{Equation 11}$$

$$\tau_{comp} = K_s(q_d - q) + D_v \frac{dq}{dt} + M(q)\frac{d^2q}{dt^2} + C\left(q, \frac{dq}{dt}\right) + G(q) \quad \text{Equation 12}$$

In Equations 11 and 12, $M(\bullet)$ is a function defined for correction of acceleration. $C(\bullet)$ is a function for reflection of Coriolis force. The other variables have been defined above with reference to Equation 10. In other words, upon implementation of a high-speed swing, the walking assistance robot 1 may determine the dynamic compensation torque $\tau_{comp}$ applied to a joint in consideration of at least one of compensation of acceleration, compensation of Coriolis force, and compensation of gravity, which may reduce resistance of the wearer against the walking assistance robot 1 during high-speed walking.

Figure 7:
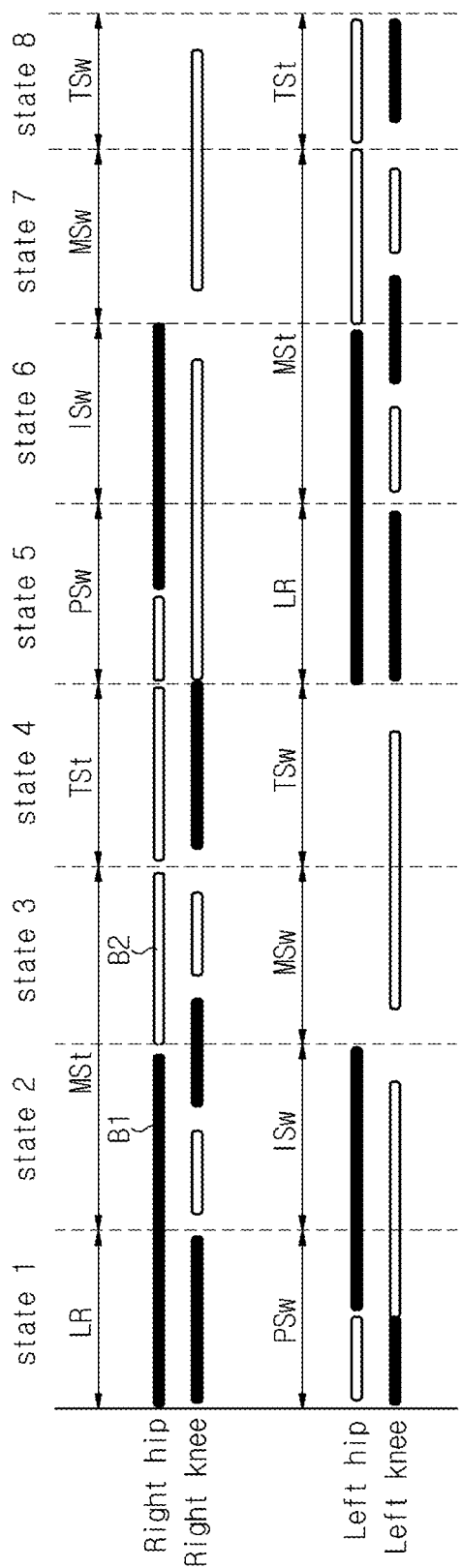
FIG. 7 is an explanatory view of one embodiment of calculated movement information.

FIG. 7 is an explanatory view of some example embodiments of calculated movement information.

As described above, to control the walking assistance robot 1, the motion state determiner 17b and the control instruction producer 17c may determine current motion continuously or periodically at a prescribed interval, and produce a prescribed control signal based on the determined result. In addition, to control each joint, such as e.g., a left hip joint, a right hip joint, a left knee joint, and a right knee joint, the motion state determiner 17b and the control instruction producer 17c may determine motion of each joint individually, and produce an individual control signal based on the determined result. As such, motions of the left and right hip joints and the left and right knee joints are continuously determined in all walking phases, and movement information is calculated based on the determined motions. FIG. 7 shows an example of the determined result based on the calculated movement information. In FIG. 7, black lines B1 designate sections in a positive work state and white lines B2 designate sections in a negative work state.

With reference to FIG. 7, motion states of different joints, e.g., the right hip joint and the right knee joint may be differently determined as shown, for example, in the second walking phase s2. In addition, even in the case of the same joint, e.g., in the case of the hip joint, a motion state thereof may be differently determined in each walking phase, e.g., according to the first walking phase s1 to the eighth walking phase s8.

Accordingly, different control signals may be produced per the drive unit 21, 31 or 41 corresponding to each joint, and different assistance torques may be applied to each joint to assist walking. As a result, the walking assistance robot 1 may apply an appropriate assistance torque on a per joint basis, which may maximize walking assistance benefits.

The actuator 18 shown in FIG. 3 is a device to convert, e.g., electric energy into other kinds of energy, e.g., dynamic energy. The actuator 18 may drive or control the respective elements of the walking assistance device 2, e.g., the first to third drive units 21, 31 and 41 based on a control signal transmitted from the processing unit 17.

According to embodiments, the main body device 10, as shown in FIG. 3, may further include the control pattern database 19. The control pattern database 19 may store various control patterns to assist the walking assistance robot 1. The control pattern database 19 may be stored in a storage device that is mounted in the housing 10a. The storage device may be a disc storage device that stores data via magnetization of a magnetic disc surface, or may be a semiconductor memory device that stores data using various kinds of memory semiconductors.

Hereinafter, a method of controlling a walking assistance robot will be described with reference to FIGS. 8 and 9.

FIG. 8 is a flowchart showing some example embodiments of a method of controlling a walking assistance robot.

With reference to FIG. 8, in operation S100, the sensing units 25, 35 and 45 of the walking assistance robot 1 may sense motion of at least one joint. The sensing units 25, 35 and 45 may directly measure the motion of at least one joint of the wearer, or may sense the motion of the joint by sensing operation of each structure 20, 30 or 40. The sensing units 25, 35 and 45 may sense motion on a per joint basis. According to some example embodiments, the at least one joint may include at least one of a hip joint, a knee joint, and an ankle joint of the wearer.

In operation S110, the processing unit 17 of the walking assistance robot 1 may calculate movement information related to movement of the at least one joint based on the sensed motion of the joint. According to some example embodiments, the processing unit 17 may calculate the movement information related to movement of at least one joint using Equation 2.

In operation S120, the processing unit 17 may determine a motion state of the at least one joint based on the calculated movement information. Further, in operation S130, the processing unit 17 may determine whether or not a motion state is changed. The motion state may include at least one of a positive work state and a negative work state. According to some example embodiments, if the calculated movement information has a positive value or is changed to a positive value, the processing unit 17 may determine that a motion state of a joint is in a positive work state. If the calculated movement information has a negative value or is changed to a negative value, the processing unit 17 may determine that a motion state of a joint is in a negative work state.

In operation S140, if, in operation S130, the motion state of the at least one joint is changed, the processing unit 17 of the walking assistance robot 1 may stop a current control mode of the walking assistance robot 1 and activate a new control mode. The new control mode may be decided according to a motion state of at least one joint.

In operation S150, the processing unit 17 may determine if the motion state of the at least one joint is a positive work state, and if the motion state is a positive work state, in operation S151, the processing unit 17 may switch from the current control mode to a control mode corresponding to a positive work state. The control mode corresponding to the positive work state may be an acceleration assistance mode to accelerate motion of the at least one joint. In the acceleration assistance mode, active torque $\tau_{pw}$ may be calculated by Equation 5. According to example embodiments, a weighting value, e.g., a synchronization index $W_{sync}$ may be added to the active torque $\tau_{pw}$. The synchronization index $W_{sync}$ may be calculated by Equation 9.

In operation S160, the processing unit 17 may determine if the motion state of the at least one joint is a negative work state rather than a positive work state, and if the motion state is a negative work state, in operation S161, the processing unit 17 may switch from the current control mode to a control mode corresponding to a negative work state. The control mode corresponding to the negative work state may be a deceleration assistance mode to decelerate motion of the at least one joint. In the deceleration assistance mode, damping torque $\tau_{wnw}$ may be calculated by Equation 7. According to example embodiments, a weighting value, e.g., a synchronization index $W_{sync}$ may be added to the damping torque $\tau_{nw}$.

If in operations S150 and S160, the processing unit 17 determines that the motion state of the at least one joint is neither a negative work state nor a positive work state, the walking assistance robot 1 may be operated according to the existing control mode and may output an error message. In addition, the walking assistance robot 1 may terminate control based on a positive work state and a negative work state.

Referring back to operation S130, if in operation S130, the processing unit 17 determines that the motion state of the at least one joint is not changed, the walking assistance robot 1 may be operated based on the existing control mode and, as discussed below, in some example embodiments, thereafter, dynamic compression may be applied to the determined control mode.

According to some example embodiments, after a control mode based on the motion state of the joint is decided (S151 and S161), in operation S170, the processing unit 17 may determine whether or not to implement dynamic compensation. Whether or not to implement dynamic compensation may be decided after decision of the control mode (S151 and S161), or may be decided simultaneously with decision of the control mode (S151 and S161).

If dynamic compensation is implemented, in operation S171, final assistance torque $\tau_{des}$ may be produced using dynamic compensation torque $\tau_{comp}$. The dynamic compensation torque $\tau_{comp}$ may be decided by Equation 10. If dynamic compensation is not implemented, final assistance torque $\tau_{des}$ may be equal to active torque $\tau_{pw}$ or damping torque $\tau_{nw}$. A synchronization index $W_{sync}$ as a weighting value may be added to active torque $\tau_{pw}$ or damping torque $\tau_{nw}$.

In operation S180, the processing unit 17 may repeat the above-described operations S100 to S171 during walking.

Figure 9:
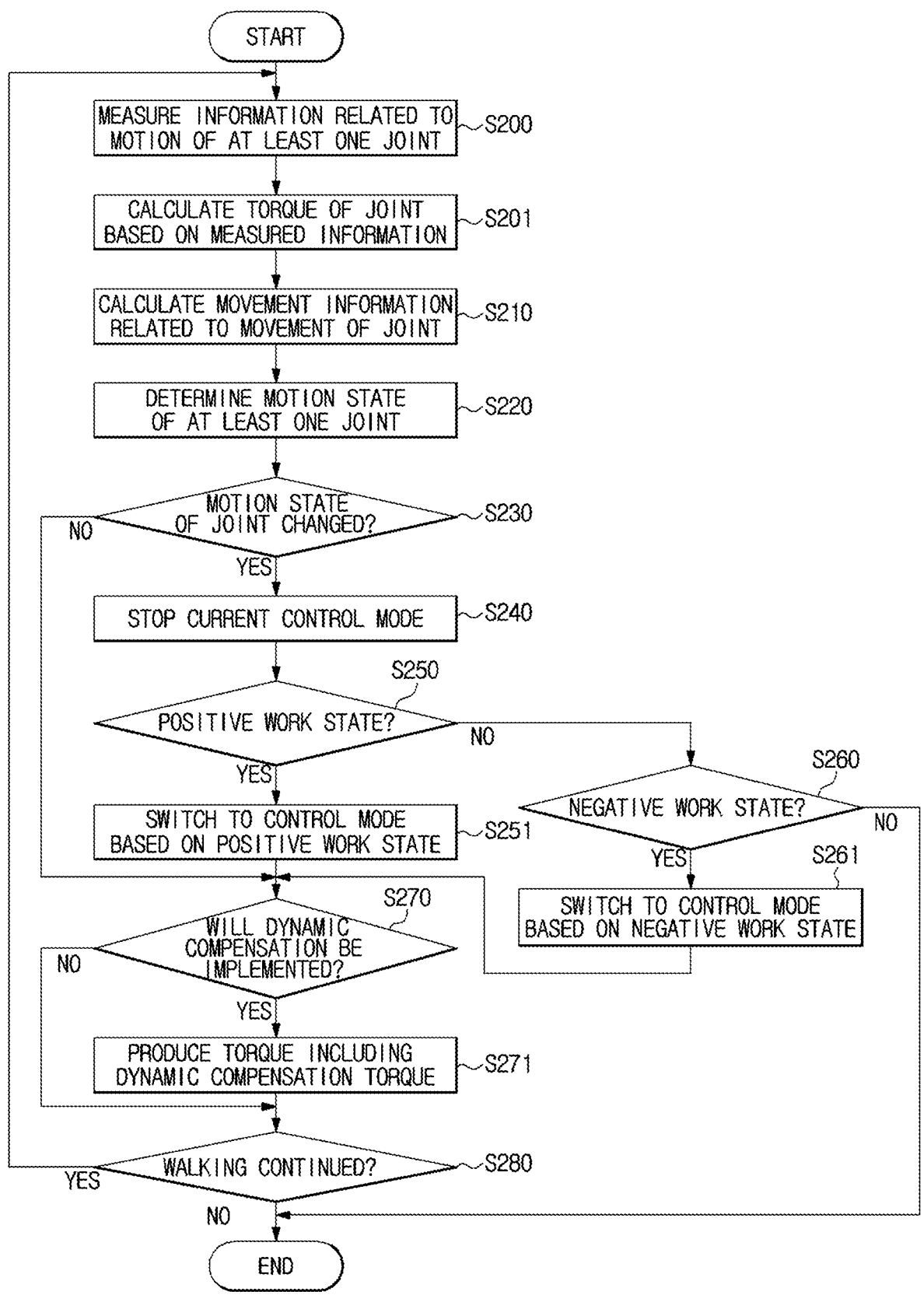
FIG. 9 is a flowchart showing one embodiment of a method of estimating motion of a joint of a walking assistance robot.

FIG. 9 is a flowchart showing some example embodiments of a method of estimating motion of a joint of a walking assistance robot.

With reference to FIG. 9, rather than sense the motion of the at least one joint in operation S100, in operation S200, the at least one measurement unit 26, 36 or 46 may measure and collect information related to motion of at least one joint corresponding to each measurement unit 26, 36 or 46. The information related to motion of at least one joint may include torque, angle, angular velocity, angular acceleration of the joint, for example. In addition, measurement time may be additionally collected.

In operation S201, the processing unit 17 of the walking assistance robot 1 may calculate torque of the joint based on the measured information. More particularly, the processing unit 17 may utilize Equation 1 to calculate torque of the joint.

As discussed in more detail below, using the calculated, torque, the processing unit 17 may perform operations S210 to S280 similar to processes S110 to S180.

In operation S210, the processing unit 17 of the walking assistance robot 1 may calculate movement information related to movement of the at least one joint using the calculated torque of the joint, and in operation S220 may determine a motion state of the at least one joint using the calculated movement information.

If the motion state of the at least one joint is changed (S230), a current control mode to control the walking assistance robot 1 may stop (S240). If the determined motion state is a positive work state (S250), the control mode of the walking assistance robot 1 may be switched to a control mode corresponding to the positive work state (S251). If the determined motion state is a negative work state (S260), the control mode of the walking assistance robot 1 may be switched to a control mode corresponding to the negative work state (S261). The control mode corresponding to the positive work state may be the above-described acceleration assistance mode. The control mode corresponding to the negative work state may be the above-described deceleration assistance mode.

According to whether or not dynamic compensation is implemented (S270), assistance torque $\tau_{es}$ including or not including dynamic compensation torque $\tau_{comp}$ may be produced (S271). If dynamic implementation is not implemented, assistance torque $\tau_{des}$ may be equal to the above-described active torque $\tau_{pw}$ or the above-described damping torque $\tau_{nw}$. Here, a synchronization index $W_{sync}$ as a weighting value may be added to the active torque $\tau_{pw}$ or damping torque $\tau_{nw}$.

In operation S280, the processing unit 17 may repeat the above-described operations S200 to S271 during walking.

As is apparent from the above description, with a walking assistance robot and a method of controlling the walking assistance robot, appropriate force is applied to muscles or joints of a wearer who wears the walking assistance robot, which allows the wearer to naturally walk without inconvenience due to the walking assistance robot.

With the walking assistance robot and the method of controlling the walking assistance robot, appropriate force is applied to the wearer at appropriate time, which may maximize walking assistance benefits.

With the walking assistance robot and the method of controlling the walking assistance robot, appropriate force is applied to muscles or joints of the wearer during walking, which may reduce energy exertion of the wearer.

Further, it may be possible to accurately sense and estimate, on a per joint basis, a positive work period and a negative work period which greatly vary according to walking speeds or environmental change.

Furthermore, owing to more efficient walking assistance in terms of energy, energy consumption of the walking assistance robot may be reduced, which may allow the walking assistance robot to implement walking assistance for a long time.

In addition, reduction in the energy consumption of the walking assistance robot may cause reduction in the size and mass of a battery for the walking assistance robot, and consequently reduction in the mass of the walking assistance robot. In this way, wearing inconvenience of the wearer due to the mass of the walking assistance robot may be reduced.

Although some example embodiments have been shown and described, it would be appreciated by those skilled in the art that changes may be made in the embodiment without departing from the principles and spirit of the example embodiments, the scope of which is defined in the claims and their equivalents.

What is claimed is:

1. A walking assistance robot comprising:
    at least one joint;
    a housing configured to accommodate an element to control the walking assistance robot;
    a waist fixing member configured to fix the housing to a waist of a wearer of the walking assistance robot;
    a support member configured to be fixed to the wearer's upper leg by a fixing member; and
    a processor configured to control movement of the walking assistance robot based on a motion state of torque of the at least one joint to assist the wearer of the walking assistance robot with walking, and to decelerate a motion of the at least one joint when the motion of the at least one joint is in a negative work state while limiting a rate of deceleration of the walking of the wearer by setting a magnitude of a damping component of the torque proportional to an angular velocity of the at least one joint and in a direction opposite to a direction of the angular velocity of the at least one joint.

2. The walking assistance robot according to claim 1, further comprising:
    a motion detector including at least one of a sensor configured to sense a motion of the at least one joint and measure information related to the motion of the at least one joint,
        wherein the sensor includes at least one of a joint angle sensor, a gradient sensor, an accelerometer, a ground reaction force (GRF) sensor, and an inertial measurement unit.

3. The walking assistance robot according to claim 2, wherein the processor is configured to determine a change in the motion state of the at least one joint based on the sensed or measured motion of the at least one joint.

4. The walking assistance robot according to claim 2, wherein the processor is configured to collect motion information related to the motion of the at least one joint associated with at least one point in time, the motion information including at least one of an angle of the at least one joint, the angular velocity of the at least one joint, an angular acceleration of the at least one joint, a walking speed of the walking assistance robot, and a ground reaction force (GRF) exerted by a ground on the walking assistance robot.

5. The walking assistance robot according to claim 2, wherein the processor is configured to calculate power or work of the at least one joint based on the torque of the at least one joint.

6. The walking assistance robot according to claim 2, wherein the processor further configured to,
    determine the motion state of the at least one joint based on a sign of the power or work of the at least one joint, and
    calculate the torque of the at least one joint such that the torque selectively includes different combinations of an active component and the damping component based on the motion state determined based on the sign of the power or work.

7. The walking assistance robot according to claim 1, wherein the processor is configured to determine if the at least one joint is in a positive work state or the negative work state based on the sensed or measured motion of the at least one joint.

8. The walking assistance robot according to claim 7, wherein the processor is configured to calculate movement information related to the sensed or measured motion of the at least one joint.

9. The walking assistance robot according to claim 1, wherein the processor is further configured to control the movement of the walking assistance robot based on the torque of the at least one joint by,
    accelerating the motion of the at least one joint when the motion of the at least one joint is in a positive work state.

10. The walking assistance robot according to claim 9, wherein the processor is configured to accelerate the motion by applying an active component of the torque to the at least one joint, the active component of the torque determined using a torque variation pattern calculated based on previous motion of the at least one joint.

11. The walking assistance robot according to claim 10, the processor is configured to determine the torque variation pattern based on a time a walking stage changed from a previous walking state to a current walking state, information regarding a torque variation position, and information regarding maximum joint torque in the current walking state.

12. The walking assistance robot according to claim 10, wherein a weighting value based on similarity of a walking period between the wearer and the walking assistance robot is added to the active component of the torque applied to the at least one joint upon acceleration of the motion.

13. The walking assistance robot according to claim 9, wherein the processor is configured to decelerate the motion by applying the damping component of the torque or the damping component of the torque reflecting a weighting value to the at least one joint, the damping component of the torque based on the angular velocity of the at least one joint, and the weighting value based on similarity of a walking period between the wearer and the walking assistance robot.

14. The walking assistance robot according to claim 9, wherein at least one of accelerating the motion and decelerating the motion includes additionally applying a dynamic compensation torque to the at least one joint.

15. The walking assistance robot according to claim 1, wherein the at least one joint includes one or more of a hip joint, a knee joint, and an ankle joint.

* * * * *